United States Patent
Pedrazzini

(10) Patent No.: US 10,024,875 B2
(45) Date of Patent: Jul. 17, 2018

(54) APPARATUS FOR MOVING AND TESTING BIOLOGICAL SAMPLES

(71) Applicant: Inpeco Holding Ltd., Qormi (MT)

(72) Inventor: Gianandrea Pedrazzini, Paradiso (CH)

(73) Assignee: INPECO HOLDING LTD., Qormi, QRM (MT)

(*) Notice: Subject to any disclaimer, the term of this patent is extended or adjusted under 35 U.S.C. 154(b) by 0 days.

(21) Appl. No.: 15/127,079

(22) PCT Filed: Mar. 13, 2015

(86) PCT No.: PCT/EP2015/055265
§ 371 (c)(1),
(2) Date: Sep. 19, 2016

(87) PCT Pub. No.: WO2015/140059
PCT Pub. Date: Sep. 24, 2015

(65) Prior Publication Data
US 2017/0097371 A1    Apr. 6, 2017

(30) Foreign Application Priority Data

Mar. 17, 2014  (IT) ............................... MI2014A0433

(51) Int. Cl.
G01N 35/02    (2006.01)
G01N 35/04    (2006.01)
G01N 35/00    (2006.01)

(52) U.S. Cl.
CPC ......... G01N 35/04 (2013.01); G01N 35/0099 (2013.01); G01N 35/026 (2013.01); G01N 2035/0415 (2013.01); G01N 2035/0465 (2013.01); G01N 2035/0472 (2013.01)

(58) Field of Classification Search
CPC ......... G01N 35/026; G01N 2035/0415; G01N 2035/0472
See application file for complete search history.

(56) References Cited

U.S. PATENT DOCUMENTS

2005/0196320 A1* 9/2005 Veiner .................... G01N 35/04
                                                          422/63
2006/0216198 A1* 9/2006 Koike .................. G01N 35/026
                                                          422/65
2010/0303590 A1 12/2010 Pedrazzini
(Continued)

FOREIGN PATENT DOCUMENTS

WO    2004/013640 A1    2/2004
WO    2013/099538 A1    7/2013

OTHER PUBLICATIONS

International Search Report, dated May 27, 2015 (3 pages).
Written Opinion of the International Searching Authority, dated May 27, 2015 (6 pages).

*Primary Examiner* — Paul West
(74) *Attorney, Agent, or Firm* — Jacobson Holman, PLLC.

(57) ABSTRACT

An apparatus for moving and testing biological samples is described, comprising a laboratory automation system for moving transporting devices of single test tubes containing biological material samples, a testing module of said biological material samples contained in said test tubes adapted to receive linear containers of a plurality of test tubes arranged in a series of consecutive housings along a line, and an interconnection module between said laboratory automation system and said testing module.

4 Claims, 6 Drawing Sheets

(56) References Cited

U.S. PATENT DOCUMENTS

2012/0058010 A1    3/2012   Pedrazzini
2013/0142596 A1    6/2013   Murakami
2014/0294699 A1   10/2014   Akutsu et al.
2016/0244269 A1*   8/2016   Akutsu ................. G01N 35/04

* cited by examiner

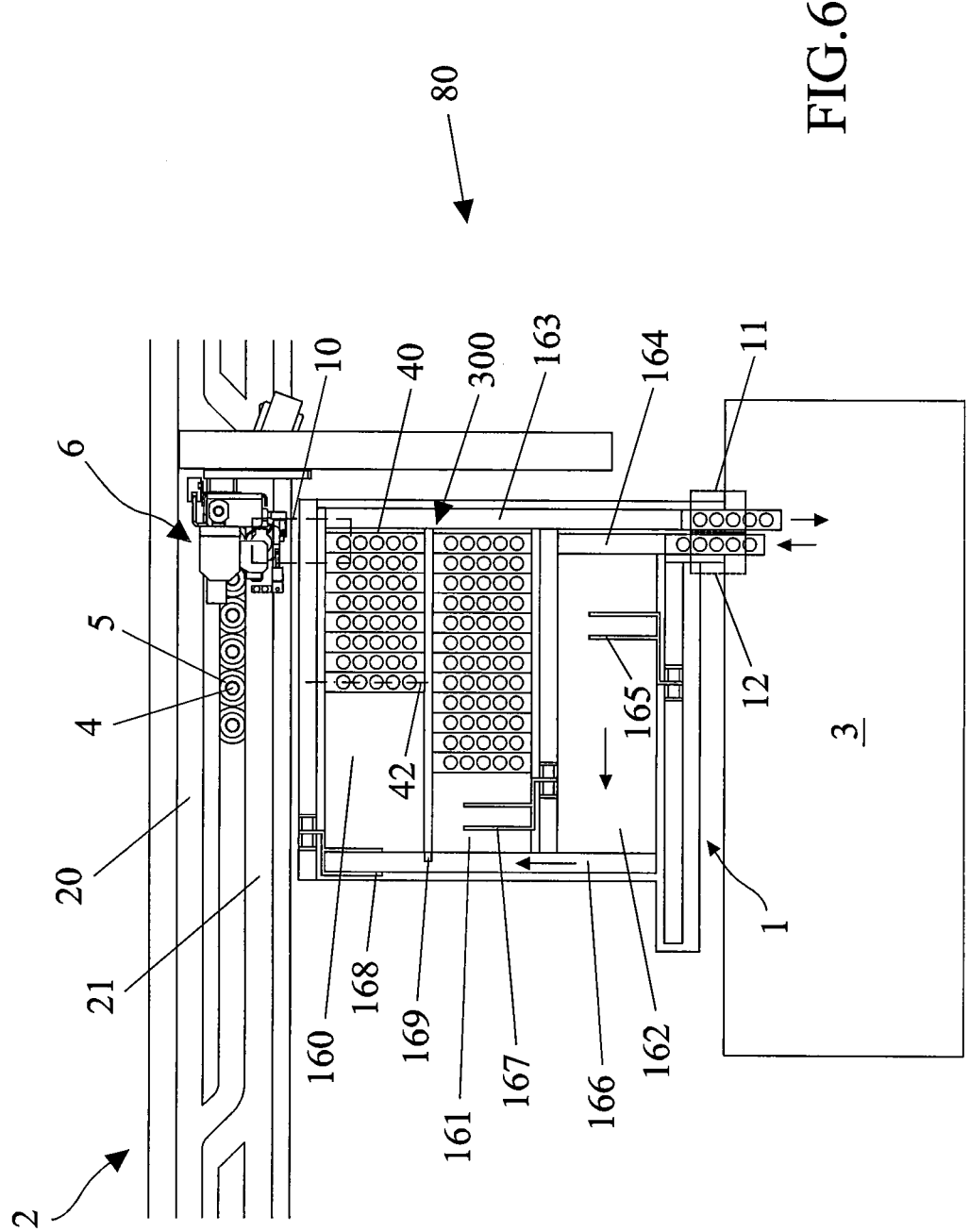

APPARATUS FOR MOVING AND TESTING BIOLOGICAL SAMPLES

The present invention relates to an apparatus for moving and testing biological samples.

BACKGROUND OF THE INVENTION

In modern laboratories, a plurality of testing modules is present, each of which is designed to carry out a predetermined type of testing on the biological samples which are routed thereto.

Obviously, more than one module of the same type may be present in the same laboratory, but, in addition to the different arrangement of the machines which may occur according to the needs of the single laboratory, a basic configuration always includes the connection of all the testing modules, arranged at different locations, with a single automation system responsible for the transport of biological samples, typically contained in test tubes supported by transporting devices, from one location to another inside the laboratory.

In addition, this automation system is also interfaced with other devices, referred to as pre or post-testing devices, which process the biological sample prior to or after the actual testing carried out by the modules, respectively.

Generally, the mechanism for passing a sample from the automation system along which it is traveling to a testing module which has to receive it, and vice versa, includes implementing a suitable interconnection between the automation system and the testing module, so that the transfer of samples occurs in the most suitable manner, irrespective of the varying configuration and geometry of the testing module itself.

WO-2008/043393 of the present Applicant describes an automation system comprising a conveyor for a plurality of transporting devices, each supporting a single test tube, and units for transferring said transporting devices from said automation system into testers of biological material contained in said test tubes. Said transfer units allow the single test tubes to be inserted directly into the testers without removing them from the respective transporting devices.

U.S. Pat. No. 6,019,943 shows a double lane for moving linear containers of a plurality of test tubes between different testing modules in series, which are encompassed between the accumulation portions of the linear containers of a plurality of test tubes.

U.S. Pat. No. 6,117,392 shows a module from transferring the linear containers of a plurality of test tubes from/to different testing modules arranged in series encompassed between the accumulation portions of the linear containers of a plurality of test tubes.

U.S. Pat. No. 6,520,313 describes an automation system, comprising a conveyor for a plurality of transporting devices, each supporting a single test tube, and units for transferring said transporting devices from said automation system to picking areas of said test tubes from said transporting devices, and for placing them into adjacent testing modules. Said transferring units allow single test tubes to be inserted into the testers by removing them from the respective transporting devices immediately close to the testing modules.

US-2013/0142596 describes an apparatus adapted to transfer test tubes between a linear container of a plurality of test tubes and an array box of test tubes on a bench adapted to store the test tubes.

BRIEF SUMMARY OF THE INVENTION

It is the object of the present invention to provide an apparatus for moving and testing biological samples, comprising an interconnection module between an automation system adapted to move transporting devices of single test tubes, and testing modules adapted to receive linear containers of a plurality of test tubes at their inlet.

It is a further object of the invention the fact that said interconnection module is efficient in managing said entering and exiting containers, thus reducing the residence time of the containers in the interconnection module.

It is a still further object of the invention the fact that said interconnection module has moving mechanisms and a geometry which are compatible with the testing module.

These and other objects are achieved by an apparatus for moving and testing biological samples as described in claim 1.

BRIEF DESCRIPTION OF THE SEVERAL VIEWS OF THE DRAWINGS

These and other features of the present invention will become more apparent from the following detailed description of embodiments thereof, shown by way of illustrative, non-limiting example in the accompanying drawings, in which:

FIG. 6 is a top plan view of a third embodiment of the interconnection module.

DETAILED DESCRIPTION OF THE INVENTION

An apparatus 80 for moving and testing biological samples comprises a laboratory automation system 2 and a testing module 3 of biological material samples.

Figure 1:
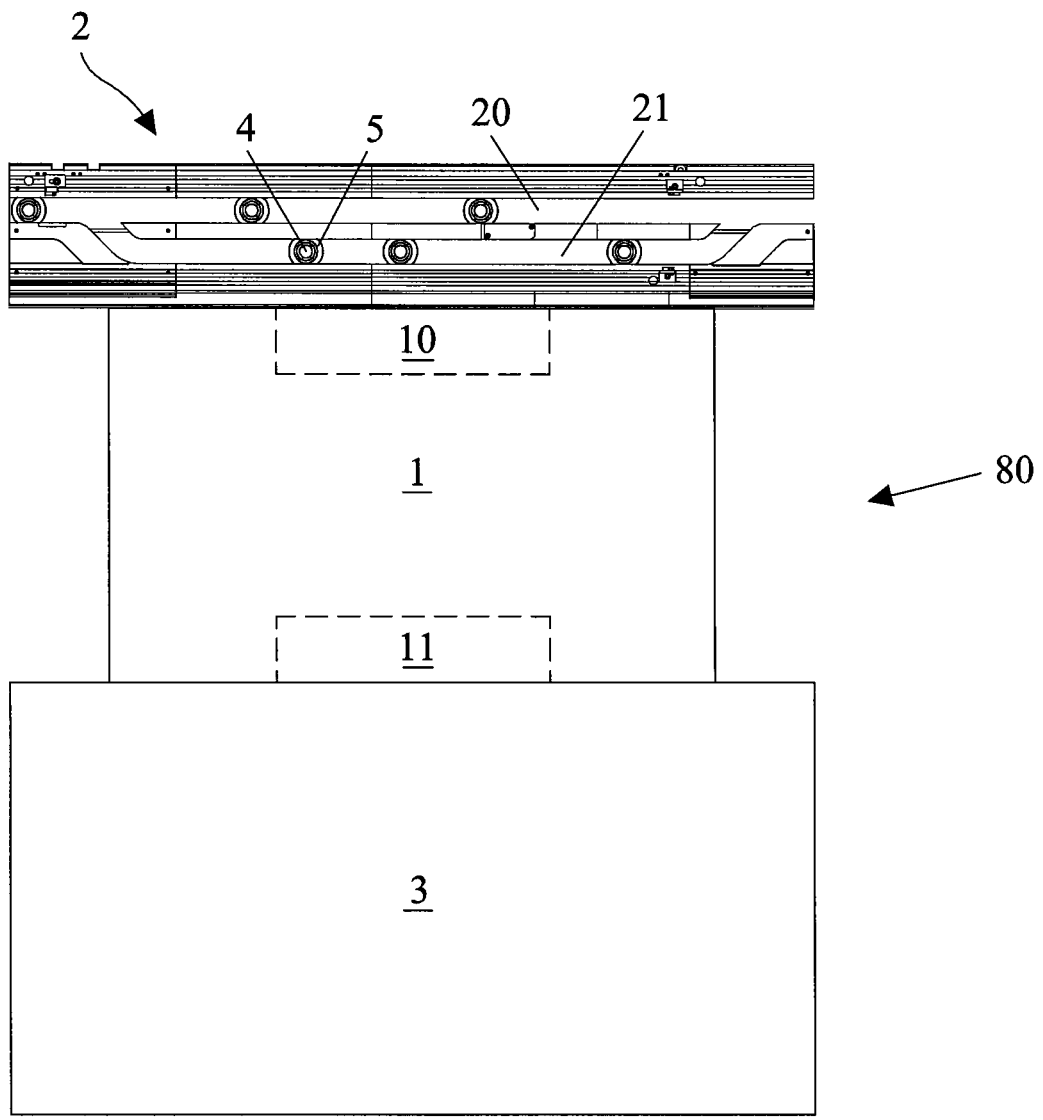
FIG. 1 is a diagrammatic top plan view of an apparatus according to the invention.

Said apparatus 80 further includes an interconnection module between the laboratory automation system 2 and the testing module 3 of biological material samples (FIG. 1).

The automation system 2 is a system for automatically identifying, transporting and routing samples which is already known in the field of laboratory automation, in view, for example, of the European patent EP-2225567 granted to the present Applicant. The biological samples run on system 2, which samples are contained in test tubes 4, in turn inserted into the transporting devices 5 of single test tubes 4.

The testing module 3, according to the constructional features and operating cycle thereof, can process a single sample at a time, hence a single test tube 4, or it can simultaneously process a hatch of a variable number of test tubes 4, inserted into the testing module 3 in specific linear containers 40 of a plurality of test tubes 4 (FIGS. 2-6).

Figure 3:
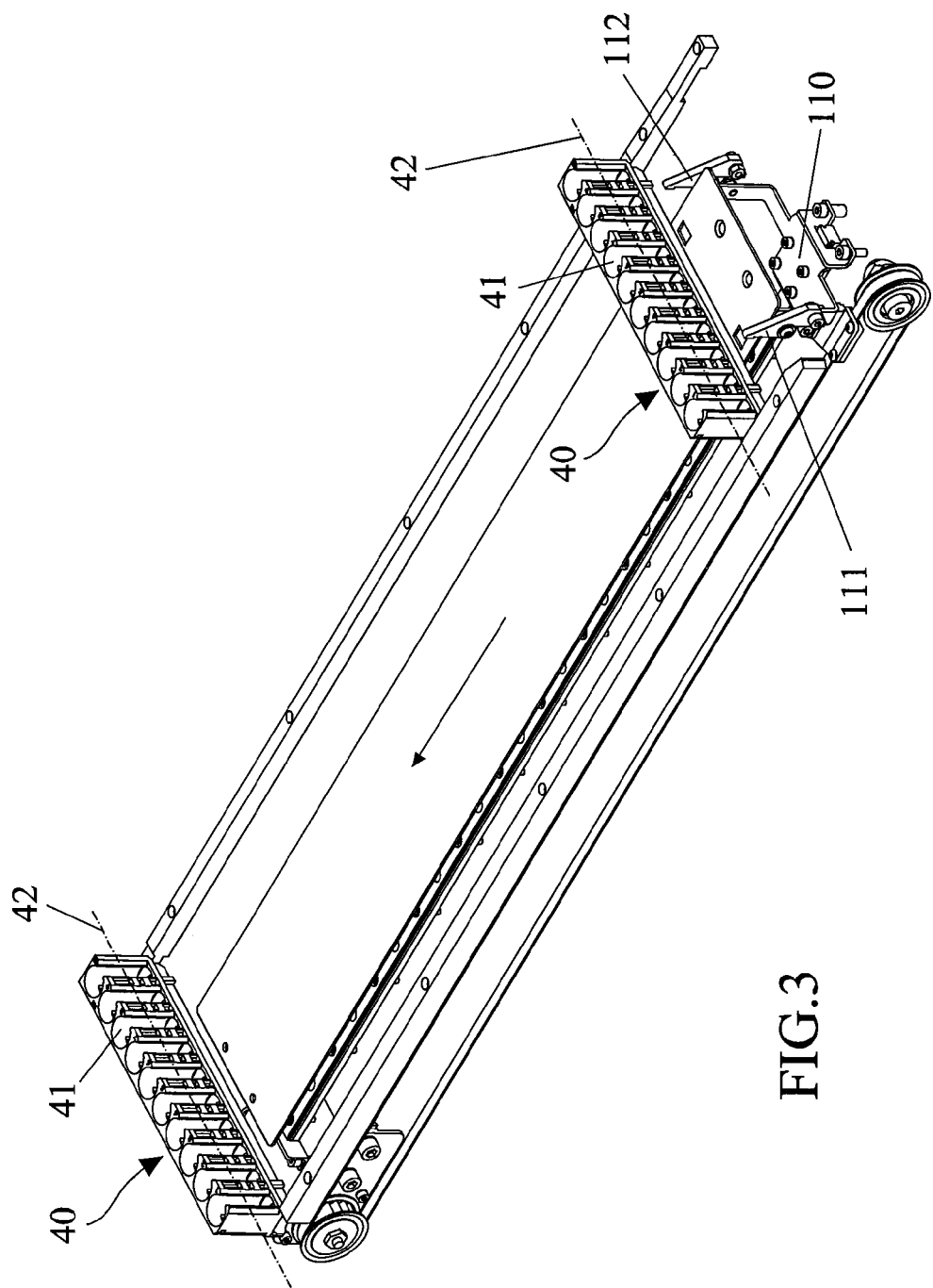
FIG. 3 is a perspective view of a moving device of linear containers of test tubes encompassed in the interconnection module in FIG. 2.
Figure 4:
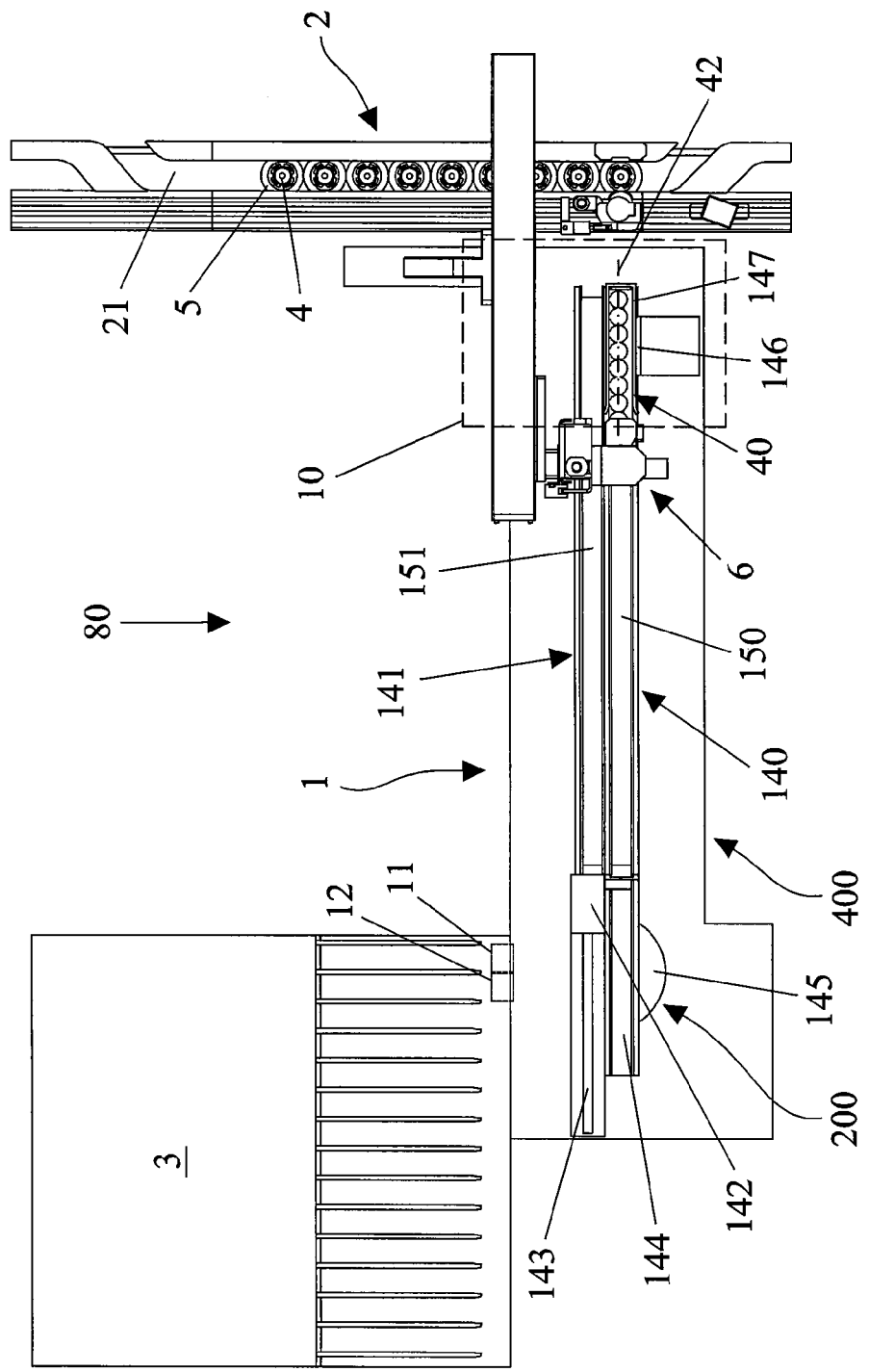
FIGS. 4, 5 are two top plan views of two different operating steps of a second embodiment of the interconnection module.

With linear container 40 of a plurality of test tubes 4 is meant a means which includes a series of consecutive housings 41 along a line 42 for test tubes 4, for example, ten test tubes 4 as shown in FIG. 3.

The interconnection module 1 is configured as a transit and sorting area, which moves the test tubes 4 when transiting from the automation system 2 to the testing module 3 and vice versa.

The test tubes 4 are redirected along the automation system 2 from a main lane 20 to a secondary lane 21, up to the interface with the interconnection module 1.

The test tubes 4 are then placed on the interconnection module 1 at a general inlet point 10. The path followed by the test tubes 4 along module 1 varies according to different possible configurations, which will be disclosed below. The transit of the test tubes 4 along module 1 ends at the outlet point 11 of the interconnection module 1, which presents a linear container 40 of a plurality of test tubes 4 to the testing module 3.

In the following discussion different embodiments of the interconnection module 1 are shown; the differences between the several embodiments shown are substantially determined by the need to adapt the geometry of the interconnection module 1 to the different types of testing modules 3 to which the samples must be routed.

Figure 2:
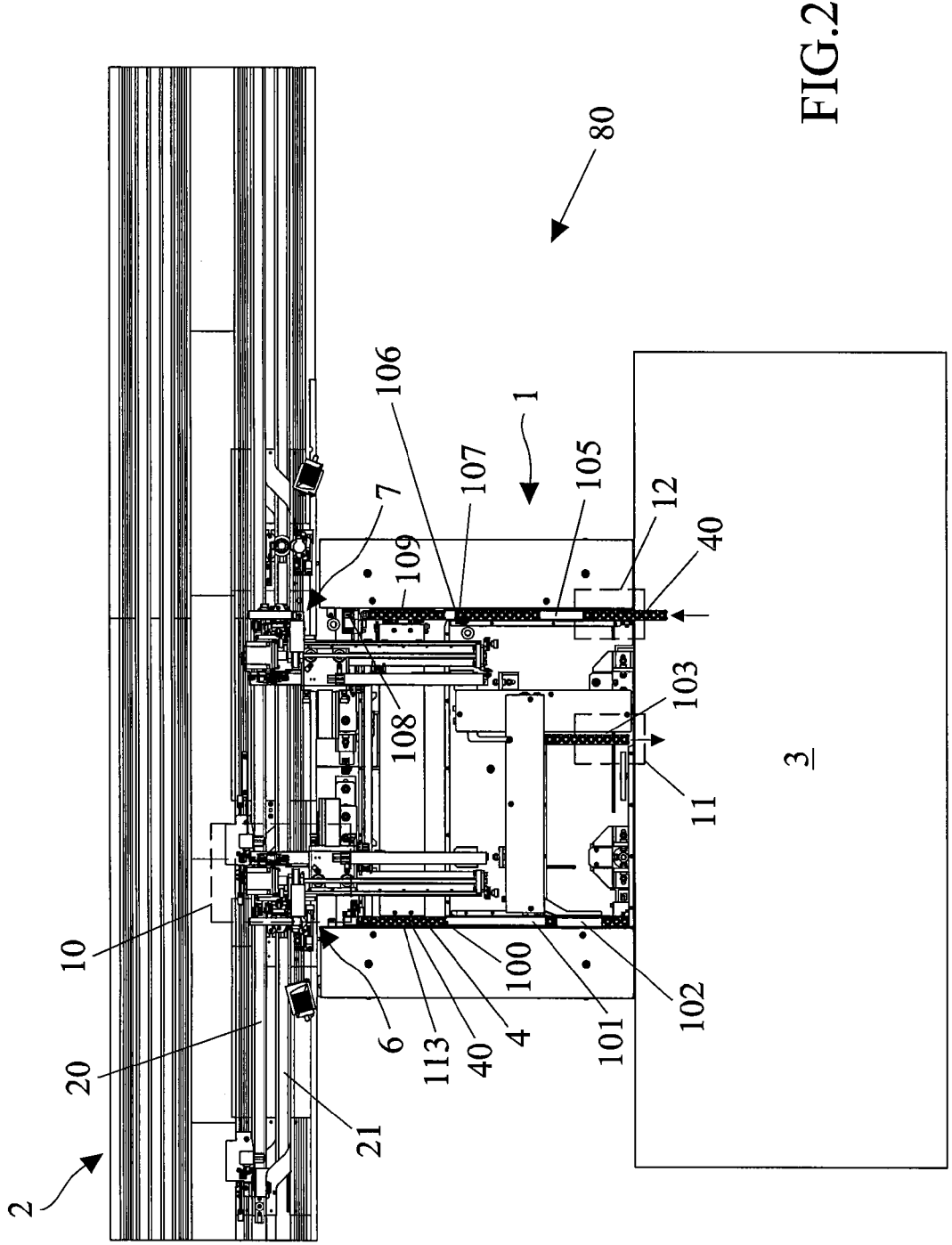
FIG. 2 is atop plan view of a first embodiment of an interconnection module.

A first embodiment is shown in FIG. 2, in which the linear container 40 of test tubes 4 is depicted in different positions in accordance with the next steps of displacing it along module 1.

The interconnection module 1 comprises a device 6 for gripping the test tubes 4, arranged at the inlet point 10 for picking the single test tubes 4 from the respective transporting devices 5 which are stationary along the secondary lane 21 of system 2 and for placing them in the housings 41 of the linear container 40 of test tubes 4 waiting on module 1, blocked by a pneumatic pusher 100. Once the linear container 40 has been completely filled through multiple consecutive cycles of picking the test tubes 4 from system 2, the release thereof is controlled by retracting pusher 100. Of course, the release may also occur, if needed, when the linear container 40 is not completely filled.

The linear container 40, once it has been released, slides along a conveyor belt 101 in the direction of line 42 along which the housings 41 of the series of test tubes 4 come in sequence, up to the opposite end, lengthwise, of module 1. Here, a shifter 102 (FIG. 3) provides for displacing the linear container 40 in a direction orthogonal to said line 42 from an end to the other, widthwise, of module 1, until it abuts against a wall 103. At this point, a pusher 104 (not visible in FIG. 2) feeds the linear container 40 into the testing module 3, at the outlet point 11 from the interconnection module 1 coincident with the inlet point of the testing module 3, The entire linear container 40 which moves with a translating motion in the direction of said line 42 enters the testing module 3.

Once the processing of the samples has been completed by the testing module 3, the linear container 40 is reinserted into module 1, in this case through a re-inlet point 12 separated from the above-mentioned outlet point 11, A conveyor belt 105 then transports the linear container 40 in the direction of line 42 up to a partition 106 which, where needed, (e.g., if there is already another linear container 40 downstream, which the former would hit) temporarily blocks the linear container 40, which is meanwhile detected by a sensor 107. At some point, the retraction of partition 106 is activated, and the linear container 40 can slide, again along belt 105 in the direction of line 42, and can come back along the end of module 1 facing system 2.

A sensor 108 detects the possible presence of test tubes 4 within the linear container 40; if such test tubes 4 are present, a gripping device 7 picks them in sequence from the linear container 40, placing them onto transporting devices 5 waiting along the automation system 2. Instead, if an empty linear container 40 should arrive, the gripping device 7 is not activated.

The linear container 40, when in an empty state, i.e., sensor 108 no longer detects the presence of any test tubes 4, has to be sent back to the inlet point 10, where supposedly a line of containers 40 always ready to receive new test tubes 4 from system 2 must always be available.

Therefore, the linear container 40 is fed in a direction orthogonal to line 42 over a short length by a pusher 109, and then coupled by a packer 110 comprising two teeth 111 and 112 (FIG. 3). Such a packer 110 just continuously moves from one side to the other of module 1, along the direction indicated by the arrow in FIG. 3, i.e., orthogonal to the line 42 of the linear container 40; because of their particular shape, the two teeth 111 and 112 are passive in their movement from left to right (with respect to FIG. 3), while being dragging in the opposite direction, since they abut against the base of the linear container 40, thus dragging it. This is how the containers 40 are compacted towards the inlet point 10.

It is worth noting that, in order to prevent an undue compacting of the containers 40 from hindering the release of the linear container 40 just filled at the inlet point 10 (discussed above), an unpacker 113 (FIG. 2) is arranged, which slightly divides the linear container 40 just filled from all the others in the line to its rightside, in order to promote the appropriate routing thereof along the conveyor belt 101.

A second embodiment includes the gripping device 6 which, once again, picks single test tubes 4 from the transporting devices 5 of single test tubes 4 along the automation system 2, to place them in a linear container 40 of test tubes 4 waiting at the inlet point 10 of the interconnection module 1, here comprising a platform 400 having two lanes 140 and 141 for running the linear containers 40 along the conveyor belts 150 and 151 (FIG. 4) in the direction of the line 42 of the same linear container 40.

In particular, lane 140 is intended to slide the just-filled linear container 40 of test tubes 4 picked by the automation system 2.

At the end of the sliding along lane 140, the linear container 40 couples to a block 142, sliding along a rail 143 so as to feed the linear container 40 into a suitable seat 144. At this point, a rotating disc 145 helps to rotate rail 143 and seat 144, integral with each other, counterclockwise by 90°.

Rail 143, seat 144 and rotating disc 145 form a roto-translating assembly 200.

Block 142 then feeds the linear container 40 with a translating motion in the direction of line 42 at the outlet point 11 of the interconnection module 1 towards the testing module 3.

Once the linear container 40 has entered the testing module 3, it is uncoupled from block 142, thus promoting the final taking of the linear container 40 by the testing module 3.

At this point, the roto-translating assembly 200 slightly translates in the direction of the lanes 140, 141 and in the translation direction of the belts 150, 151 (FIG. 5), so that seat 144 now faces a re-inlet point 12, from which a linear container 40 from the testing module 3 comes.

Such a linear container 40 is, in turn, coupled by block 142, and fed with a translating motion into seat 144. The subsequent clockwise 90 rotation of the rotating disc 145 allows to arrange the linear container 40, housed in seat 144, so that it faces the lane 141 in which the linear container 40 itself is then translated in the direction of line 42 by virtue of the action of block 142, finally to slide by virtue of the underlying conveyor belt 151 again in the direction of line 42.

The linear container 40 then remains waiting at lane 141, blocked by a gate; this may occur because, e.g., in the inlet point 10, the filling of a new linear container 40 with test tubes 4 from system 2 may be underway. When such a filling is completed, and the just-filled linear container 40 is released, the space at the inlet point 10 is cleared, and thus a pusher 146 pushes a guide 147 attached thereto in a direction orthogonal to the lanes 140, 141, until the guide faces lane 141. The subsequent retraction of the gate releases the linear container 40 in line, which is thereby received by guide 147.

Since pusher 146 and guide 147 are glued to each other, when pusher 146 is retracted towards the initial position, it drags along guide 147 and hence the linear container 40 inserted therein, which is thereby located at the inlet point 10.

If the above-mentioned linear container 40 is full of test tubes 4, they are thus discharged from the gripping device 6 into the transporting devices 5 waiting along the automation system 2; each housing 41 of the linear container 40 from which the test tube 4 has been just picked up, may be immediately filled by the immediate transfer of a new test tube 4 from the automation system 2 to the housing 41, which is now empty, of the linear container 40.

Figure 5:
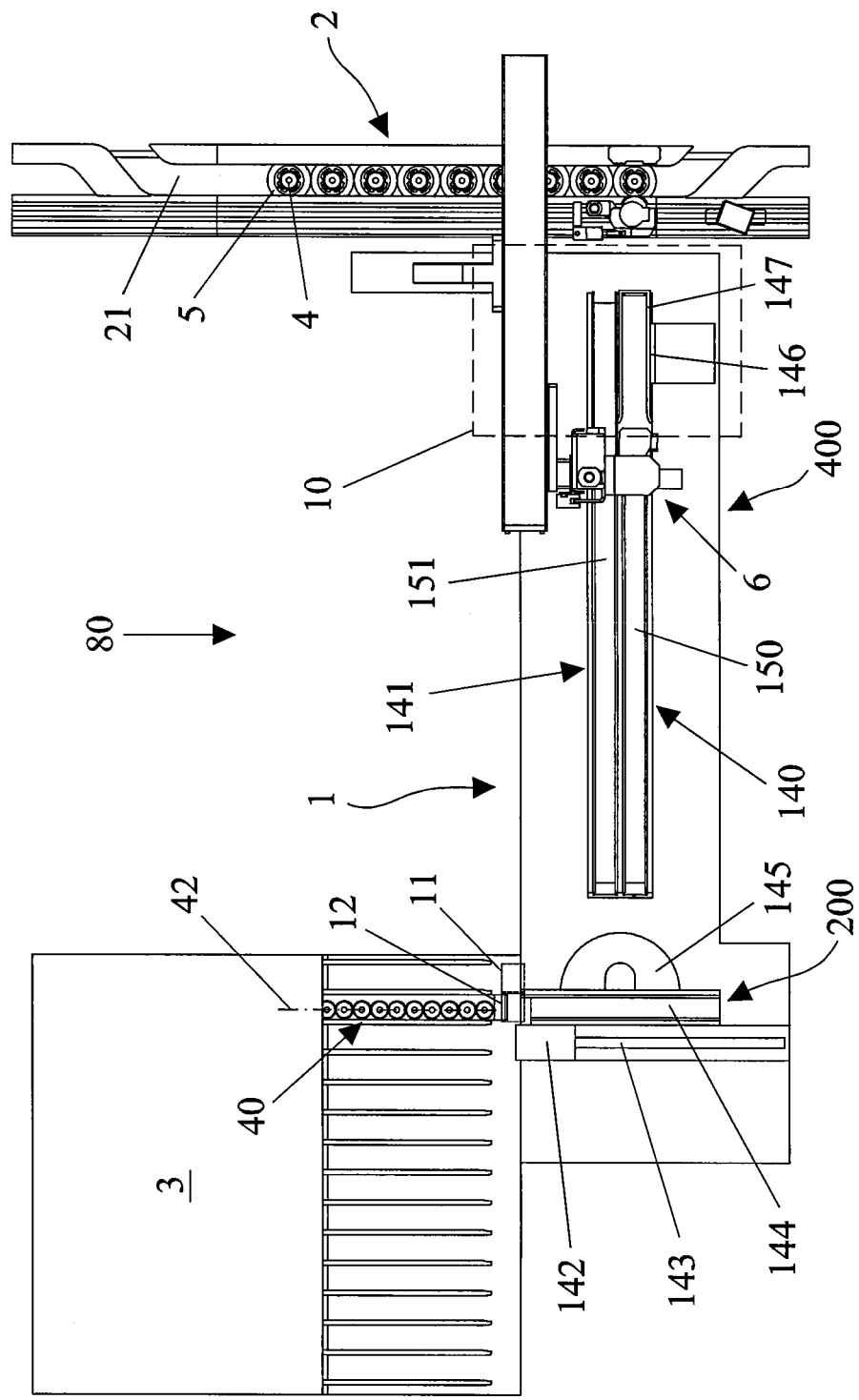

It is worth noting that the containers 40 may be loaded from platform 1 to testing module 3, and vice versa, indiscriminately (by virtue of the above-mentioned translation of the roto-translating assembly 200) at one of the outlet 11 and re-inlet 12 points indicated in FIGS. 5, 6; in essence, in this embodiment, each of the two points 11 and 12 can be either the "outlet" or the "re-inlet" point, in different steps of the cycle of loading/unloading containers 40 into/from the testing module 3.

In a third embodiment, the interconnection module 1 comprises a platform 300 adapted to move linear containers 40 of test tubes 4 intended to receive, at the inlet point 10 of module 1, single test tubes 4 picked from transporting devices 5 of single test tubes 4 along the automation system 2 by the gripping device 6, and placed by the latter into the different housings 41 arranged along the line 42 of the linear container 40 (FIG. 6).

Platform 300 has several lanes (three in the embodiment shown) 160, 161, 162, the first two 160, 161 typically housing two different sets of containers 40, each designated to receive test tubes 4 which come in mutually different types. On the contrary, there is no accumulation of containers 40 on the lane 162 closest to the testing module 3; in fact, it only acts as a transit lane of the containers 40 themselves.

Once the filling of a linear container 40 located either in the lane 160 or 161 has been completed, it is released and routed along a conveyor belt 163, which transports it with a translating motion in the direction of the line 42 of the linear container 40 towards the outlet point 11, at which the translational insertion of the linear container 40 in the testing module 3 occurs.

Once the linear container 40 has been processed inside the testing module 3, it goes back to the interconnection module 1, through the re-inlet point 12 and by sliding along a conveyor belt 164, again with a translating motion in the direction of the line 42 thereof.

At this point, the linear container 40 is inserted into a guide 165 adapted to house it and feed it along lane 162 in a direction orthogonal to the line 42 of the linear container 40. At the end of the latter, the presence of a further conveyor belt 166 provides for feeding, the linear container 40 again towards system 2 along the line 42, to be then coupled by a guide 167 or a guide 168, intended to redirect the linear container 40 along lane 161 or 160 in a direction orthogonal to line 42, respectively.

The choice of the redirecting along lane 160 or 161 is dictated by the type of test tubes 4 housed by the linear container 40 (in essence, it is the same lane from which the linear container 40 was previously released towards the testing module 3). If the linear container 40 needs to be redirected along lane 161, a stop gate 169 blocks the linear container 40 so that guide 167 may conveniently receive and feed it along lane 161. On the contrary, if the linear container 40 needs to be directed towards lane 160, the stop gate 169 is retracted, so that the linear container 40 reaches the guide 168, which then feeds it along lane 160.

The linear container 40, redirected along lane 161 or 160, is fed by guide 167 or 168, respectively, and arranges in line with other containers 40 which typically are already present; in fact, as stated, each of the two lanes 160, 161 is designed to house containers 40 with test tubes 4 of a mutually different type.

Once the queue of containers preceding the linear container 40 has been cleared, it the linear container 40 located at the position where it can be accessed again by the gripping device 6, which thus picks the test tubes 4 of the linear container 40 to place them again in transporting devices 5 of single test tubes 4 waiting along system 2.

Of course, in the attempt of parallelizing the operations of loading/unloading the test tubes 4, and in accordance with the description of some of the embodiments shown above, nothing prevents the gripping device 6 from providing, in conjunction with the emptying of the linear container 40, to immediately replace the housings 41 of the linear container system 2, if these are available. On the contrary, if the linear container 40 is emptied of test tubes 4 but no new test tubes of the same type come from system 2, the linear container 40 is in any case released in an empty state from the head of lane 160 or 161, so as not to block other test tubes 4 waiting to be discharged from other containers 40 in line. Obviously, the released linear container 40 is not routed here to the testing module 3 (in fact, since it has no test tubes 4, its routing to module 3 would make no sense), but rather immediately received by guide 163 and fed along lane 162 to be arranged immediately in line again with the other containers 40 along lane 160 or 161 for future use.

It can be assumed that, in one or more of the above-described embodiments, the gripping device 6 for transporting test tubes 4 from system 2 to module 1, and vice versa, may have an inclined translational axis, in order to obviate possible height differences between the automation system 2 and the testing module 3, the height of the interconnection module 1 having to be adjusted to that of the latter.

The innovative aspect of the finding is represented by the management of the transfer of biological samples from an automation system 2 to a testing module 3, and vice versa, through an interconnection module 1 which can take different possible configurations, while the presence of elements in common between a configuration and the other being apparent.

The geometry of the interconnection module 1, as well as the elements composing it, may have an ideally infinite number of implementation variants, particularly adapting to any possible configuration of the testing module 3, both in terms of modes of entering/exiting the samples in/from the latter, and taking into account the space needs related to the dimensions of the testing module 3 itself.

In any case, whichever the applied embodiment is, a bidirectional and continuous transfer of samples is always ensured, by virtue of the suitable connection of all the modules involved, from a logical and physical point of view.

The so-devised invention is susceptible to a number of modifications and variations, all of which falling in the scope of the inventive concept.

In practice, the materials used, as well as the shapes and dimensions could be any, according to the needs.

The invention claimed is:

1. An apparatus for moving and testing biological samples, comprising:
    a laboratory automation system for moving transporting devices of single test tubes containing biological material samples;
    a testing module of said biological material samples contained in said test tubes adapted to receive linear containers of a plurality of test tubes arranged in a series of consecutive housings along a line;
    an interconnection module between said laboratory automation system and said testing module allowing the linear containers to enter/exit in/from the testing module with a translating motion in the direction of said line, said interconnection module comprising at least one gripping device of said single test tubes, for picking at an inlet point said single test tubes from said transporting devices which are stationary along a lane of said laboratory automation system, said lane being adapted to interface with said interconnection module, and for placing said single test tubes in said housings of said linear container waiting on said interconnection module, and
    transporting means adapted to move said linear containers in a direction orthogonal to said line;
    wherein said interconnection module is configured as a transit and sorting area, which moves said test tubes from said automation system to said testing module and vice versa, and comprises:
        a first conveyor belt adapted to move said linear containers along said line from the inlet point to an end point of the first conveyor belt wherein a shifter displaces the linear containers in a direction orthogonal to said line, to an outlet point of the interconnection module;
        a second conveyor belt adapted to move said linear containers along said line from a re-inlet point towards the laboratory automation system;
        a pusher adapted to continuously move empty linear containers towards said inlet point, in a direction orthogonal to said line in an opposite versus with respect to the displacement of the linear containers to the outlet point by said shifter;
        said re-inlet point being separated from said outlet point.

2. The apparatus according to claim 1, wherein said interconnection module comprises
    stop means adapted to temporarily block a linear container along said second conveyor belt so as to prevent the contact between two consecutive linear containers moving in the direction of the line on the same second conveyor belt,
    a packer adapted to compact a plurality of linear containers in a direction orthogonal to said line, and which includes two teeth being shaped so as to be passive in their movement in one direction and active in their feeding movement in the other direction, the compacting thus occurring,
    an unpacker adapted to separate two linear containers arranged side by side in correspondence of their long side to promote an appropriate routing along said first conveyor belt moving in the direction of said line of said linear container.

3. An apparatus for moving and testing biological samples, comprising:
    a laboratory automation system for moving transporting devices of single test tubes containing biological material samples;
    a testing module of said biological material samples contained in said test tubes adapted to receive linear containers of a plurality of test tubes arranged in a series of consecutive housings along a line;
    an interconnection module between said laboratory automation system and said testing module allowing the linear containers to enter/exit in/from the testing module with a translating motion in the direction of said line, said interconnection module comprising at least one gripping device of said single test tubes, for picking said single test tubes from said transporting devices which are stationary along a lane of said laboratory automation system, said lane being adapted to interface with said interconnection module, and for placing them in said housings of said linear container waiting on said interconnection module,
    characterized in that said interconnection module comprises
        one or more accumulation lanes and a transit lane of said linear containers of a plurality of said test tubes,
        guides adapted to move said linear containers along said lanes in a direction orthogonal to the line,
        a first conveyor belt adapted to move said linear containers along said line from the inlet point to an outlet point of said interconnection module;
        a second conveyor belt adapted to move said linear containers along said line from the end of the transit lane wherein the linear containers are brought from a re-inlet point, towards the laboratory automation system;
        said re-inlet point being separated from said outlet point,
        stop means arranged along said first and second conveyor belts adapted to prevent the contact between two consecutive linear containers.

4. An apparatus for moving and testing biological samples, comprising:
    a laboratory automation system for moving transporting devices of single test tubes containing biological material samples;
    a testing module of said biological material samples contained in said test tubes adapted to receive linear containers of a plurality of test tubes arranged in a series of consecutive housings along a line;
    an interconnection module between said laboratory automation system and said testing module allowing the linear containers to enter/exit in/from the testing module with a translating motion in the direction of said line, said interconnection module comprising at least one gripping device of said single test tubes, for picking said single test tubes from said transporting devices which are stationary along a lane of said laboratory automation system, said lane being adapted to interface with said interconnection module, and for placing them in said housings of said linear container waiting on said interconnection module, characterized in that said interconnection module comprises a platform having two lanes for running the linear containers along said respective first and second conveyor belts in the direction of said line of said linear container, a roto-translating assembly which includes a rail, a rotating disc, a seat and a block translating along said rail, said seat selectively facing either one of said lanes or said inlet/outlet point of the testing module, said block being adapted to be coupled to a linear container and feed it in the direction of said line either from one of said lanes into said seat, and vice versa, or into the testing module and vice versa, a pusher adapted to move a guide of a single linear container between said two lanes into a portion of the platform facing the automation system.

* * * * *